United States Patent [19]
Ahr et al.

[11] Patent Number: 6,162,454
[45] Date of Patent: *Dec. 19, 2000

[54] INSECT REPELLENT ARTICLE PROVIDING LOW CONTACT WETNESS

[75] Inventors: Nicholas Albert Ahr, Cincinnati; Robert Allen Godfroid, West Chester, both of Ohio; Anna Belle Marin, Long Branch, N.J.

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/691,197

[22] Filed: Aug. 7, 1996

Related U.S. Application Data

[60] Provisional application No. 60/013,065, Mar. 8, 1996.

[51] Int. Cl.[7] .................................................. A01N 25/34
[52] U.S. Cl. ........................... 424/411; 424/403; 424/405; 424/409; 514/919
[58] Field of Search .............................. 428/321.1, 314.2, 428/314.4, 315.5, 315.7, 315.9, 905, 134, 136; 424/402–404, 410, 416, 443, 447–449, DIG. 7, 76.2–76.4, 76.8; 514/918–920

[56] References Cited

U.S. PATENT DOCUMENTS

| | | | |
|---|---|---|---|
| 2,402,982 | 7/1946 | Steenbergen | 206/63.2 |
| 2,819,995 | 1/1958 | Wassell | 167/42 |
| 3,295,246 | 1/1967 | Landsman et al. | 43/131 |
| 3,590,118 | 6/1971 | Conrady et al. | 424/19 |
| 3,767,785 | 10/1973 | Bordenca | 424/29 |
| 3,858,807 | 1/1975 | Rabussier et al. | 239/56 |
| 3,896,995 | 7/1975 | Lelicoff | 239/36 |
| 3,929,135 | 12/1975 | Thompson | 128/287 |
| 4,131,195 | 12/1978 | Worrell, Sr. | 206/205 |
| 4,145,001 | 3/1979 | Weyenberg et al. | 239/56 |
| 4,168,000 | 9/1979 | Macritchie | 206/63.3 |
| 4,277,024 | 7/1981 | Spector | 239/36 |
| 4,283,011 | 8/1981 | Spector | 239/36 |
| 4,285,468 | 8/1981 | Hyman | 239/55 |
| 4,342,314 | 8/1982 | Radel et al. | 128/287 |
| 4,387,849 | 6/1983 | Van Loveren et al. | 239/6 |
| 4,439,415 | 3/1984 | Henneart et al. | 424/16 |
| 4,445,641 | 5/1984 | Baker et al. | 239/6 |
| 4,459,058 | 7/1984 | Bennett | 401/88 |
| 4,463,045 | 7/1984 | Ahr et al. | 428/131 |
| 4,476,171 | 10/1984 | Takeuchi | 428/38 |
| 4,529,125 | 7/1985 | Sullivan | 239/56 |
| 4,590,111 | 5/1986 | Takeuchi | 428/67 |

(List continued on next page.)

FOREIGN PATENT DOCUMENTS

| | | | |
|---|---|---|---|
| 0 260 896 A2 | 9/1987 | European Pat. Off. | A61L 9/01 |
| 0356028 | 2/1990 | European Pat. Off. | |
| WO 93/00115 | 1/1993 | WIPO | |
| WO 94/27646 | 4/1994 | WIPO | A61L 9/12 |
| 9427646 | 12/1994 | WIPO | |

OTHER PUBLICATIONS

Copy of Package of Repello–Patches™, Distributed by P.J. Maxwell, Rockford, IL.

Copy of Bioscent Fragrance Wristband, Distributed by Island Marketing, Hyde Park, NY.

*Primary Examiner*—Neil S. Levy
*Attorney, Agent, or Firm*—Joan B. Tucker; Roddy M. Bullock; David M. Weirich

[57] ABSTRACT

The present invention provides a portable, disposable article for repelling insects. The article includes a fibrous substrate which can be impregnated with the insect repellent. In one embodiment, the fibrous substrate is disposed intermediate a porous cover and a barrier layer, and comprises fibers having external capillary channels. The porous cover can comprise an apertured plastic film having tapered apertures. The insect repellent can be contained in a breakable packet, such that when the breakable packet is broken, the insect repellent is directed through the fibrous substrate for release through the apertured film.

25 Claims, 4 Drawing Sheets

6,162,454
Page 2

U.S. PATENT DOCUMENTS

| | | | |
|---|---|---|---|
| 4,614,299 | 9/1986 | Van Loveren et al. | 239/6 |
| 4,661,388 | 4/1987 | Charbonneau | 428/43 |
| 4,739,928 | 4/1988 | O'Neil | 239/45 |
| 4,750,284 | 6/1988 | Parry et al. | 40/301 |
| 4,802,626 | 2/1989 | Forbes et al. | 239/36 |
| 4,804,122 | 2/1989 | Riley | 239/56 |
| 4,842,761 | 6/1989 | Rutherford | 252/90 |
| 4,849,606 | 7/1989 | Martens, III et al. | 219/271 |
| 4,874,129 | 10/1989 | Disapio et al. | 239/36 |
| 4,881,671 | 11/1989 | Horton et al. | 224/222 |
| 4,898,328 | 2/1990 | Fox et al. | 239/45 |
| 4,915,301 | 4/1990 | Munteanu | 239/45 |
| 4,917,929 | 4/1990 | Henecke | 428/41 |
| 4,923,119 | 5/1990 | Yamamoto et al. | 239/55 |
| 4,923,745 | 5/1990 | Wolfert et al. | 428/35.4 |
| 4,932,155 | 6/1990 | Friemel et al. | 43/125 |
| 4,961,930 | 10/1990 | Pendelwitz, Jr. et al. | 424/411 |
| 5,003,635 | 4/1991 | Peterson | 2/69 |
| 5,033,122 | 7/1991 | Smith | 2/209.3 |
| 5,069,231 | 12/1991 | Rutherford | 131/335 |
| 5,071,704 | 12/1991 | Fischel-Ghodsian | 428/354 |
| 5,109,022 | 4/1992 | Jeanne et al. | 514/552 |
| 5,139,864 | 8/1992 | Lindauer | 428/304.4 |
| 5,150,722 | 9/1992 | Rutherford | 131/335 |
| 5,168,654 | 12/1992 | Chien | 43/129 |
| 5,180,107 | 1/1993 | Lindauer | 239/35 |
| 5,198,287 | 3/1993 | Samson et al. | 428/248 |
| 5,200,248 | 4/1993 | Thompson et al. | 428/131 |
| 5,221,535 | 6/1993 | Domb | 424/450 |
| 5,242,111 | 9/1993 | Nakoneczny et al. | 239/47 |
| 5,252,387 | 10/1993 | Samson et al. | 428/248 |
| 5,382,245 | 1/1995 | Thompson et al. | 604/367 |
| 5,395,047 | 3/1995 | Pendergrass, Jr. | 239/56 |
| 5,738,860 | 4/1998 | Schonfeldt et al. | 424/402 |
| 5,948,423 | 9/1999 | Karg | 424/409 |

INSECT REPELLENT ARTICLE PROVIDING LOW CONTACT WETNESS

This patent application claims priority under 35 USC 119(e) to provisional patent application 60/013,065 filed Mar. 8, 1996.

FIELD OF THE INVENTION

This invention is related to an article for providing release of a volatile substance, and more particularly, to a portable, disposable article for providing release of an insect repellent from a release surface, the release surface having a low contact wetness.

BACKGROUND OF THE INVENTION

Bug or insect repellent for personal use has been historically delivered in a number of different ways. For example, it may be sprayed or wiped onto one's skin, sprayed into one's immediate environment, and/or sprayed onto one's clothing. The bug repellent solution is typically volatile so that vapors are emitted which repel bugs away from one's body.

Absorbent substrates saturated with volatile solutions of bug repellent, made in the form of patches, have been available for application to clothing. Typically, a patch containing a volatile solution must be contained in a package which prevents vaporization of the solution prior to application of the patch. U.S. patent application 08/369,068, "Package for Containing and Applying a Bug Repellent Patch" filed Jan. 5, 1995 in the name of Cook et al, discloses a package for containing a bug repellent impregnated patch. The disclosed package enables a user, to apply the patch to a target surface without contacting the patch.

Such patches can have a barrier material between the substrate and a target surface, such as a user's clothing. The barrier material can permit greater volumes of: the volatile solution to be used to provide longer lasting protection from insects. A.-; the amount of solution is increased, however, it is more likely that some of the, solution may leak out of the substrate in liquid form, and possibly soil an item, such as the user's skin or clothing. Accordingly, the amount of solution that can be released in vapor form in a given amount of time, from a given surface area of the article, and for a given amount of liquid initially provided on the article is limited by the desire to prevent soiling of an item by liquid leaking out of the patch.

Accordingly, it is an object of the present invention to provide a portable, disposable article for providing release of a volatile liquid material, such as liquid insect repellent material.

Another object of the present invention is to provide a portable, disposable article for providing release of a volatile liquid material while minimizing the amount of the liquid material which is transferred to the wearer's skin or clothing when the article is applied to a target surface, such as by pressing.

Another object of the present invention is to provide a portable, disposable article for providing release of a volatile liquid material from a release surface of the article, wherein the release surface has a low contact wetness under a prescribed loading

SUMMARY OF THE INVENTION

The present invention comprises a disposable, portable article for providing release of volatile liquid material, such as an insect repellent material, from a release surface of the article. The article includes a substrate impregnated with the volatile liquid material. Under a prescribed loading, the release surface of the article has a contact wetness of less than about 100 mg, more preferably less than about 50 mg, and even more preferably less than about 25 mg. Under the prescribed loading, the release surface can have a normalized contact wetness of less than about 100 mg/gram, more preferably less than about 50 mg/gram, and even more preferably less than about 25 mg/gram, where the normalized contact wetness is the contact wetness divided by the total weight of the liquid material impregnating the substrate.

In one embodiment, the article can provide a normalized release rate of at least about 0.25, more preferably at least about 0.40, and even more preferably at least about 0.50.

In one embodiment of the present invention, the article comprises a barrier layer, a porous cover layer, and a substrate impregnated with a volatile liquid material. The release surface can comprise an outwardly facing surface of the porous cover layer. The article can also comprise an adhesive fastener for attaching the article to a target surface, such as a wearer's garment.

The release surface of the porous cover layer can have an open area ratio of at least about 20 percent, and more preferably at least about 30 percent to provide effective release of vapors of the volatile liquid material. In one embodiment, the open area ratio can be greater than about 50 percent. The porous cover layer can have a caliper of at least about 0.015 inch, and in one embodiment, at least about 0.050 inch.

The disposable article can have a maximum caliper no greater than about 1.0 cm, preferably less than about 5.0 mm, and more preferably less than about 3.0 mn as measured with a confining load of 32.2 grams applied by a 0.95 inch diameter load foot. The article can have a total weight of no greater than about 4.0 grants (measured as the article is applied to the target surface), and a stiffness of no more than about 0.5 lb/in, and more preferably no more than about 0.1 lb/in, to provide for comfortable conformance with a variety of target surfaces.

The substrate can be impregnated with a volatile liquid material comprising an insect repellent. In one embodiment, the substrate is impregnated with no more than about 2.0 grams of liquid material, and the ratio of the weight of the volatile liquid material to the weight of the substrate is at least about 2.0.

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

DETAILED DESCRIPTION OF THE INVENTION

Figure 1:
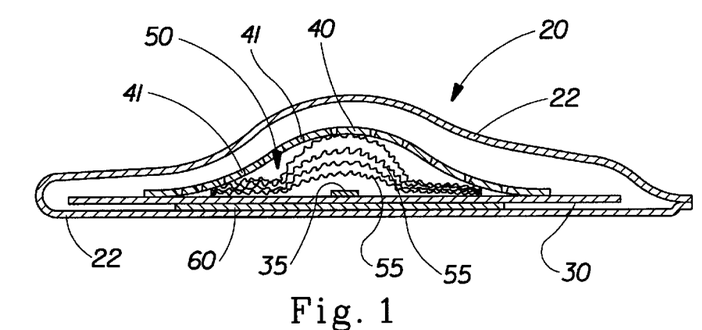
FIG. 1 is a cross-sectional view of an embodiment of the present invention wherein the article is enclosed in a sealed package.
Figure 2:
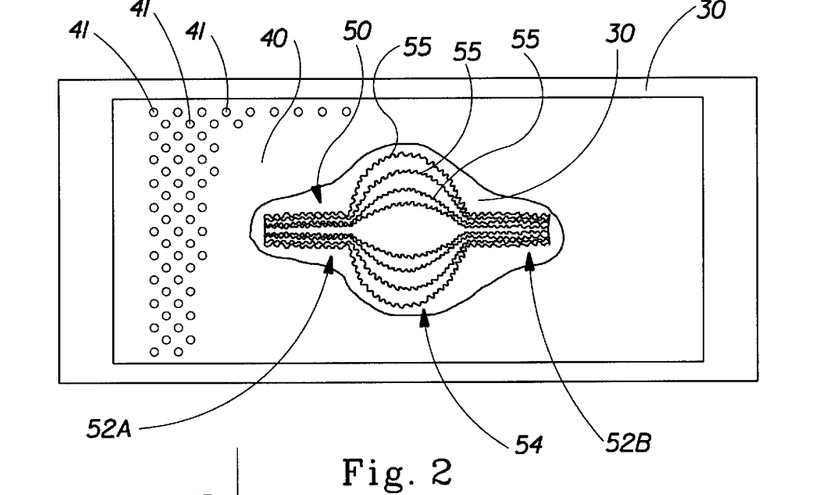
FIG. 2 is a top plan view of the article of FIG. 1, with the sealed package removed and the porous cover layer partially cut away to show a substrate having a relatively lower density region extending between relatively higher density regions.

FIGS. 1 and 2 show one embodiment of a disposable, portable article 20 according to the present invention for providing a release of volatile material comprising one or more components. The article 20 comprises a release surface and a substrate impregnated with a volatile liquid material. In one embodiment, the article 20 comprises a substrate impregnated with a volatile liquid material, and the material released comprises an insect repellent.

By the term "disposable" it is meant that the article 20 is intended to be discarded after a single use. By the term "portable" it is meant that the article 20 can be conveniently and comfortably carried in a pocket, purse, or handbag. By the term "volatile liquid material" it is meant a liquid material comprising a component having a vapor pressure of at least about 0.001 mm Hg at 50 degrees Centigrade.

In the embodiment shown in FIGS. 1–2, the article 20 comprises a barrier layer 30, a porous cover layer 40 having an outwardly facing release surface 44, and a substrate 50 impregnated with a volatile liquid material. The material with which the substrate 50 is impregnated preferably comprises a material effective for repelling insects. The release surface of the article has a contact wetness of less than about 0.100 gram (100 mg) under a prescribed loading, as described more fully below.

The article 20 can also include a fastener 60, such as a pressure sensitive adhesive. The fastener 60 can be used to support the article 20 on a target surface, such as a wearer's garment. The article 20 can be sealed in wrapper 22 to prevent evaporation of the insect repellent prior to use of the article 20. In FIG. 2 the wrapper 22 is omitted to show the internal construction of the article 20.

Referring to the components of the article 20 in more detail, the barrier layer 30 is generally impervious to the volatile liquid substance. The barrier layer 30 prevents the volatile liquid substance in the substrate 50 from contacting the target surface on which article 20 is supported. In one embodiment the barrier layer 30 comprises a flexible film, such as a polymeric film; a flexible foil; or a composite material such as a foil/polymeric film laminate. By flexible it is meant that barrier, 30 is compliant and readily conforms to the shapes and contours of a variety of target surfaces, such as clothing.

A suitable barrier layer 30 can comprise a woven or nonwoven material or a polymeric film such as thermoplastic film of polyethylene or polypropylene. A suitable thermoplastic film is a polyethylene film having a thickness of between about 0.012 mm to about 0.051 mm. Suitable films are manufactured by Clopay Corporation of Cincinnati, Ohio under the designation P18-0401 and by Ethyl Corp. of Terre Haute, Ind. under the designation XP-39385. Alternatively, the barrier layer 30 can comprise a laminate of foil and polymeric film, such as a Type M2077 foil/film laminate manufactured by the American Can Co. of Minn., Minn.

The fastener 60 can be joined directly or indirectly to the barrier layer 30, as shown in FIG. 1. Suitable fasteners 60 include, but are not limited to, adhesive fasteners and mechanical fasteners, such as VELCRO brand fasteners. Suitable pressure sensitive adhesives from which the fastener 60 can be formed are Century A-305-IV brand Adhesive manufactured by Century Adhesives Corp. of Columbus, Ohio; and Instant Lock 34-2823 brand adhesive manufactured by the National Starch and Chemical Company of Bridgewater, N.J.

The wrapper 22 can comprise a thermoplastic film incorporating a release liner for covering the fastener 60 while the article 20 is sealed in the wrapper 22. Suitable release liners for adhesive fasteners are described in U.S. Pat. No 4,917, 697, which patent is incorporated herein by reference. Non-limiting examples of suitable release liners are BL30MG-A Silox E1/0 and BL30MG-A Silox 4P/O manufactured by the Akrosil Corp. of Menasha, Wis.

The porous cover layer 40 can provide a normalized release rate of at least 0.25, and more preferably at least 0.40, while providing a low contact wetness. The method for measuring release rates and normalized release rates of the volatile substance from the article 20 are described below.

The porous cover layer 40 can comprise a film formed of a liquid impermeable material. A plurality of apertures 41 extend through the film. In one preferred embodiment, the porous cover layer can comprise an apertured formed plastic film having a release surface in the form of an outwardly facing surface 44. The porous cover layer 40 also has an inwardly facing surface 42.

In one embodiment, apertured formed plastic films are preferred because they are generally non-absorbent with respect to the volatile liquid substance and help prevent the volatile liquid material from passing through the cover layer 40 to contact the wearer's skin or clothing.

The porous cover layer 40 can be joined to the barrier layer 30, either directly or indirectly, by a number of suitable methods. In the embodiment shown in FIG. 1, the perimeter of the cover layer 40 can be secured directly to the barrier layer 30 by adhesives, heat and/or pressure sealing, ultrasonic bonding, and the like. A suitable heat sealing method is disclosed in U.S. Pat. No. 5,382,245 issued Jan. 17, 1995 to Thompson et al.

The porous cover layer can have a caliper 45 of at least about 0.005 inch. The caliper 45 is measured under a compressive load of 32.2 grams using a circular load foot having a 0.95 inch diameter (about 0.1 psi). The caliper 45 provides separation of the liquid in the substrate 50 from the outwardly facing surface 44 of: the porous cover layer 40. Such a caliper 45 helps to restrict the liquid in the substrate 50 from reaching the surface 44, and possibly contacting the wearers skirt or clothing. In one embodiment, the caliper 45 can be at least about 0.010 inch, and more preferably at least about 0.015 inch, and even more preferably at least about 0.050 inch.

Figure 3:
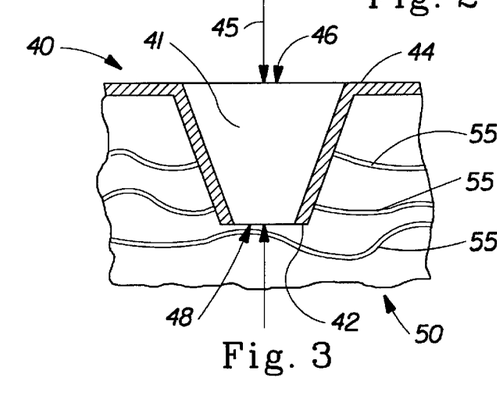
FIG. 3 is a enlarged cross-sectional view of a portion of the article of FIG. 1 showing a porous cover layer having generally conically shaped apertures.

The apertures 41 can also be shaped to restrict flow of the liquid from the substrate 50 to the outer surface 44. As shown in FIG. 3, the apertures 41 can bee tapered from a relatively large base opening 46 at the outwardly facing surface 44 to a relatively smaller apex opening 48 at the inwardly facing surface 42. U.S. Pat. No 3,929,135 issued Dec. 30, 1975 to Thompson is incorporated herein by reference for the purpose of disclosing a suitable formed film having tapered openings. In an alternative embodiment not shown, the apertures 41 can be tapered from a relatively large opening at the inward surface 42 to a relatively smaller apex at the outward surface 44.

The openings 46 can each have a surface area between about 0.015 square mm and about 32 square mm. The porous cover layer 40 can have an open area ratio of at least about 10 percent. In one embodiment, the porous cover layer 40 has an open area ratio of at least about 20 percent, more preferably at least about 30 percent, and even more preferably at least about 50 percent. For instance, a suitable porous cover layer 40 can have an open area ratio between about 20 percent and about 50 percent. Such an open area ratio is suitable for providing effective release of the volatile material from the substrate.

The open area ratio is determined by first measuring the total surface area of the porous cover layer 40 overlying the substrate 50, as viewed in FIG. 2, including the area of the openings 46. The surface areas of the openings 46 overlying the substrate are then measured and added. The surface area is measured at the outwardly facing release surface 44. The open area ratio is the ratio of the sum of the areas of these openings 46 divided by the total surface area of the cover layer 40 overlying the substrate 50.

While the porous cover layer 40 is shown having tapered apertures 41 in FIGS. 1–3, it will be understood that other formed films can also be used to provide release of the volatile material from the article 20, while restricting flow of the liquid volatile material from the substrate 50 to the surface 44. Other formed films which can make suitable cover layers 40 are disclosed in the following U.S. Patents, which are incorporated by reference herein: U.S. Pat. No 4,324,246 issued to Mullane et al; U.S. Pat. No. 4,342,314 issued to Radel et a.; U.S. Pat. No. 4,463,045 issued to Ahr et al.; U.S. Pat. No. 4,629,643 issued to Curro et al.; and U.S. Pat. No 5,006,394 issued to Baird. One suitable porous cover layer 40 is marketed as DRI-WEAVE by The Procter & Gamble Company on sanitary napkins.

In yet another embodiment, the porous cover layer 40 can comprise a relatives large aperture formed film (LAFF). Such a LAFF film can be formed to have it generally three dimensional character from a generally planar sheet of polyethylene, having a nominal thickness of about 1.5 mils (0.0015 inch). The LAFF film can be formed to have discrete apertures 41 disposed in a generally continuous network surface 44. The LAFF porous cover layer 40 can have tapered apertures 41 with base openings 46 ranging in size from about 0.007 square inch to about 0.015 square inch. The LAFF cover layer 40 can have a caliper of at least about 0.050 inch, and can have an open area ratio of at least 20 percent, more preferably at least 30 percent, and in some embodiments, greater than 50 percent. One suitable LAFF cover layer 40 can have an open area ratio of about 38 percent, and a caliper of between about 1.6 and about 1.7 mm (0.063 inch to about 0.067 inch). A suitable LAFF porous cover layer is available from Tredegar Industries under the designation X5870.

In still another embodiment, the porous cover layer 40 can comprise a sheet of MOLDEX brand apertured polyvinyl alcohol sheet material, available from Moldex Metric Inc. of Culver City, Calif. Such an apertured sheet has discrete apertures 41 disposed in a generally continuous network surface 44. The MOLDEX apertured sheet material can have a caliper of at least about 2.0 mm (0.079 inch), and can have an open area ratio of about 36 percent.

The substrate 50 can be fibrous, and can be in the form of a woven or non-woven patch, batt, tow, tuft, or bundle of a fibers. The fibers can be absorbent (e.g. cellulosic fibers or other natural fibers) or non-absorbent with respect to the volatile liquid substance. By "non-absorbent" it is meant that when the substrate 50 is immersed in the volatile liquid substance, the individual fibers absorb an amount of the volatile liquid substance less than their own weight (less than one gram of the volatile liquid substance absorbed by the fiber per gram of fiber weight).

Accordingly, the volatile liquid substance is stored in the interstitial space between fibers or along the fibers' surfaces, rather than inside the fibers themselves, thereby enhancing release of the volatile liquid substance from the substrate 50.

In one embodiment, the substrate can comprise fibers formed from a polymer such as polyolefin. Suitable fibers include but not limited to polyethylene, polypropylene, and polyester fibers. The substrate 50 can be joined, directly or indirectly, to the barrier layer 30. In the embodiment shown in FIG. 1, the substrate 50 is secured directly to an inwardly facing surface of the barrier layer 30 by a layer of adhesive 35. Suitable adhesives 35 include Findley Adhesive #2120 or Findley H2031 Adhesive available from Findley Adhesives, Inc. of Elmgrove, Wis., and Century 5227 Adhesive available from Century International Adhesive and Coating Corp. of Columbus, Ohio.

Figure 4:
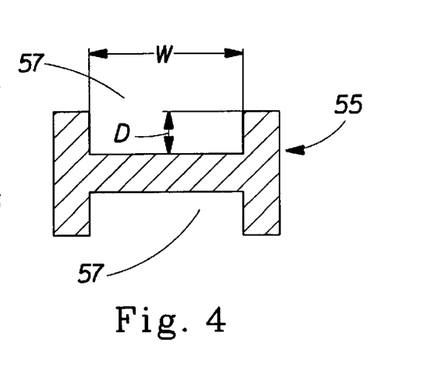
FIG. 4 is a a cross-sectional illustration of a capillary channel fiber having a generally I-shaped cross section.

In another embodiment, the substrate 50 can comprise a plurality of capillary channel fibers 55. Capillary channel fibers 55 are fibers that have one or more channels formed therein, preferably on their exterior surfaces. FIG. 4 shows a capillary channel fiber 55 having a generally I-shaped cross-section. It will be understood that suitable capillary channel fibers 55 can have any number of shapes, including but not limited to I, H, C, V, and U-shaped cross-sections. The channels 57 in the exterior surfaces of the fiber 55 can have a width W and a depth D. The value of W can be between about 10 microns and about 100 microns. The value of D can be between about 10 microns and about 100 microns. The capillary channel fibers 55 can have a denier of between about 10 and about 45 grams/9000 meters of fiber length. Suitable capillary channel fibers 55 are disclosed in the following references, which are incorporated herein by reference: U.S. Pat. No 5,382,245 issued Jan. 17, 1995 to Thompson et al.; and U.S. Pat. No. 5,200,248 issued Apr. 6, 1993 to Thompson et al.

The value of W can be greater than or equal to the value of D. In one embodiment, the ratio of W/D can be at least about 1.5, and more preferably at least about 2.0. Such relatively shallow channels 57 having a relatively high W/D ratio are capable of transporting the volatile substance while providing for enhanced release of the substance from the substrate 50 compared to the release that would be provided with fibers 55 having channels 57 with lower W/D ratios. In one embodiment tire value of D can be between about 15 microns and about 30 microns, and the value of W can be between about 40 microns and about 70 microns.

The substrate 50 can comprise a relatively high density region and a relatively low density region. The relatively high density region provides relatively rapid transport of the volatile fluid throughout the substrate, while the relatively lower density region promotes relatively rapid release of the volatile liquid material from the substrate. The fibers in at least a portion of the substrate 50 can be oriented in a predetermined direction, and in one embodiment the fibers in at least a portion of the substrate 50 are arranged in a generally parallel fashion to provide wicking of the volatile liquid in a predetermined direction.

Referring to FIG. 2, the substrate 50 can comprise a relatively low density region 54 extending between and joining two relatively high density regions 52A and 52B. The fibers in the relatively high density regions 52A and 52B can be arranged in a generally parallel fashion to provide wicking of the volatile liquid substance into the relatively low density region 54. The substrate shown in FIG. 2 can be formed from a length of generally parallel capillary channel fibers 55. The length of generally parallel capillary channel fibers can be compressed to buckle a portion of the fibers radially outwardly, thereby forming the relatively low density region 54.

In another embodiment, the substrate 50 can comprise a natural or synthetic sponge material, or an open celled foam material. Suitable open celled foams, such as foams prepared by polymerizing a high internal phase emulsion, are described in the following U.S. Patent documents, which are incorporated herein by reference: U.S. patent application Ser. No. 08/370,695, Absorbent Foams Made From High Internal Phase Emulsions Useful For Acquiring and Distributing Aqueous Fluids, filed Jan. 10, 1995 in the name of Stone, et al.; U.S. patent application entitled Absorbent Foams Made From High Internal Phase Emulsions Useful For Acquiring Aqueous Fluids, filed Aug. 30, 1995 in the name of DesMarais; U.S. Pat. No. 5,147,345; High Efficiency Absorbent Articles for Incontinence Management, issued Sep. 15, 1992 in the name of Young et al.

Figure 6:
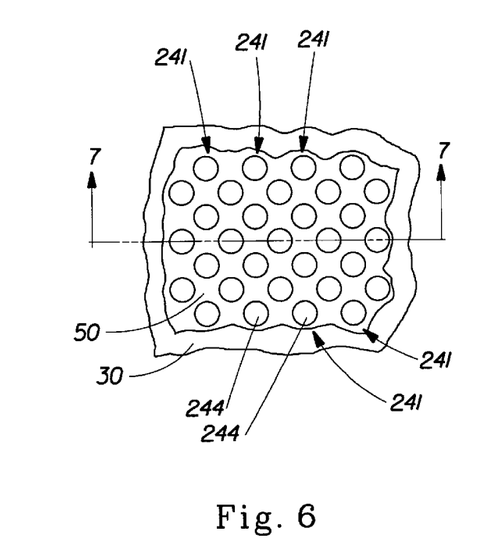
FIG. 6 is a plan view of an alternative embodiment of the present invention having discrete stand-offs extending from the substrate to provide a release surface comprising a continuous network opening.
Figure 7:
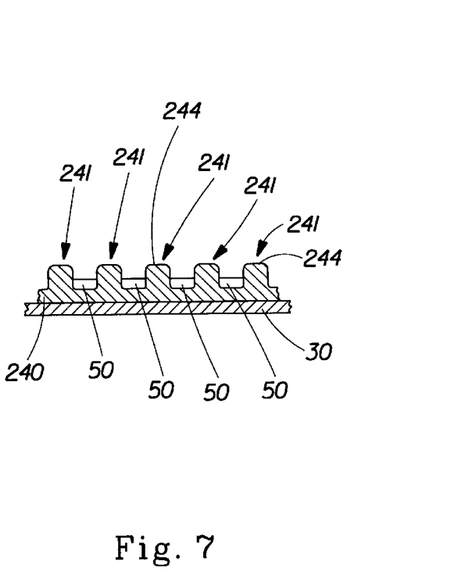
FIG. 7 is a cross-sectional view of the article of FIG. 6 taken along lines 7—7, and showing the discrete stand-offs extending from a surface of the substrate.

In the embodiments described above, the release surface comprises a surface of a porous cover layer 40, wherein the porous cover layer 40 comprises a plurality of discrete apertures in a generally continuous network surface 44. Alternatively, the release surface could comprise discrete surfaces forming a generally continuous network opening. For instance, the release surface could be formed by discrete stand-offs extending from the substrate 50, such as in the form of pegs or other protuberances. Referring to FIGS. 6 and 7, the stand-offs are designated by numerals 241.

The discrete stand-offs 241 have surface portions 244 which are disposed above the surface of the substrate 50, and define the release surface. The stand-offs 241 are formed to be capable of resisting deformation, such as by a finger-tip, which could result in contact of the skin with the substrate 50. The spacing between the stand-offs 241 permits release of the volatile material from the substrate 50. Together, the discrete standoffs 241 provide a load resistant release surface with a generally continuous network shaped opening from which vapors of the volatile material in the substrate 50 can escape.

The stand-offs 241 can have any number of shapes or configurations, including but not limited to spherical, cylindrical, mushroom, conical, and combinations thereof Alternatively, the stand-offs can comprise elongated elements, such as in the form of straight or curvilinear line segments. As shown in FIG. 7, the stand-offs 241 can extend through the substrate 50 and be integral with, or attached to, a base sheet 240. The base sheet 240 can be integral with, or attached to, the barrier 30. The fibers of the substrate 50 can be entangled about the stand-offs 241, such as by hydroentanglement, or can be otherwise forced into the spaces between the stand-offs 241.

Figure 9:
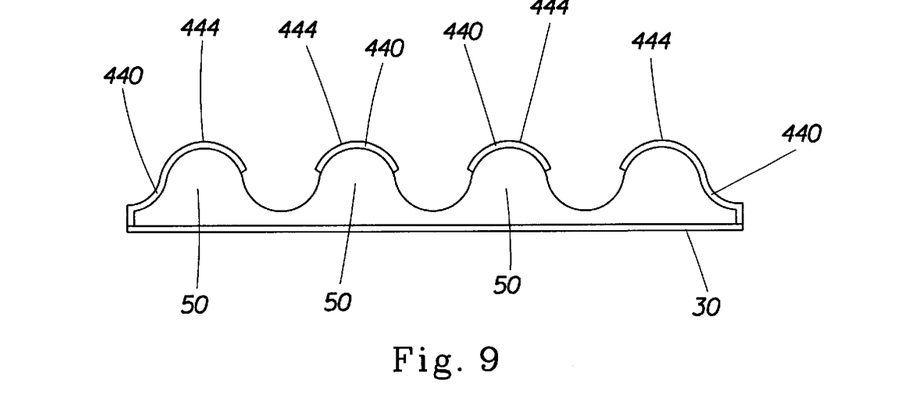
FIG. 9 is a cross-sectional view of an alternative embodiment of the present invention wherein the substrate has a contoured surface, and wherein a barrier layer is applied to elevated portions of the contoured surface to provide a release surface which is integral with the substrate.

In still another embodiment, the release surface can be formed integrally with the substrate 50, such as by applying a barrier layer to a contoured surface of the substrate 50. Referring to FIG. 9, the substrate 50 can have a contoured surface comprising a plurality of ridges or other protrusions, such that a portion of the contoured surface is elevated with respect to other portions of the contoured surface. In FIG. 9, the substrate 50 has a corrugated surface comprising peaks and valleys. The substrate can be formed to have a contoured surface in any suitable manner, such as by molding a web of fibers, or by folding a sheet of fibers to have accordion like pleats.

A barrier layer 440 can be applied to selective portions of the contoured surface, such that elevated portions of the surface of the substrate 50 are coated by the barrier layer, while other portions of the surface of the substrate remain uncoated. In FIG. 9, the peaks are coated with the barrier layer 440, while the valleys remain uncoated. The barrier layer can comprise a curable resin-like material which is substantially impervious to the liquid material.

The peaks are formed to be capable of resisting deformation, such as by a finger-tip, which could result in contact of the skin with uncoated portions of the substrate 50. The coated peaks and uncoated valleys provide a load resistant release surface which is integral with the substrate 50, and which permits vapors of the volatile material in the substrate 50 to escape. The height of the peaks and the stiffness of the substrate 50 are selected to provide low contact wetness on the barrier layer 440 under a prescribed loading.

The material with which the substrate 50 is impregnated preferably comprises one or more components effective in repelling bugs, including but not limited to insects such as mosquitoes. Of course, in other embodiments it may desirable to impregnate the substrate with a material which provides a desired scent, regardless of its suitability as an insect repellent.

Generally, suitable materials with which the substrate can be impregnated include materials having a boiling point between about 140 degrees. Centigrade to about 290 degrees Centigrade, and in one embodiment between about 230 Centigrade to about 260 Centigrade. Suitable materials can have a molecular weight between about 75 and about 300, and in one embodiment, a molecular weight between about 146 and about 257.

In one embodiment, the substrate 50 can be impregnated with a liquid is material comprising one or more organic compounds. Such organic compounds can have between one carbon atom and 20 carbon atoms (C1–C20 organic compounds), and more preferably, between 6 carbon atoms and 12 carbon atoms (C6–C12 organic compounds). In one embodiment, the substrate 50 is impregnated with a liquid material comprising one or more C6–C12 organic compounds. Such organic compounds can be saturated, unsaturated, or aromatic, and can have straight carbon chains, branched carbon chains, or cyclical structures.

Examples of suitable organic compounds include, but are not limited to, alkanes, alkenes, alcohols, such as citronellol;

aldehydes, such as citronellal; ketones; esters; amides, phenols, nitriles, and lactones. One suitable mixture with which the substrate 50 can be impregnated is CITRONELLA CEYLON, designated Fit FDG, FP 138 by International Flavors and Fragrances Inc. of New Jersey. Other suitable materials with which the substrate 50 can be impregnated include but are not limited to Ethyl Butylacetylaminopropionate; N,N diethyl-M-toluamnide (DEET); and Dimethyl Phthalate.

Still other examples of a suitable liquid material which can used to impregnate the substrate 50 include mixtures of one or more of the following ingredients: GERALDEHYDE (trademark of OFF, generically 5,9-dimethyl-4,8-decadienal); Citronellyl nitrile; Thyme oil red, Eugenol, Citral (generically 3,7-dimethyl-2,6-Octadien-1-al); Gamma methyl ionone; Beta Phenethyl alcohol; Clove bud oil; APO PATCHONE (trademark of IFF, generically Para-Isopropylcyclohexanol), Limonene PFG (generically p-Mentha-1,8-diene); PEOMOSA (trademark of IFF, generically 4-methyl-betaphenylethyl alcohol), and/or VIOLIFF (trademark of IFF, generically 4-Cyclooctenyl methyl carbonate). One suitable liquid material which can be used to impregnate the substrate 50 comprises a mixture, on a weight percent basis, of about 0 percent to about 5 percent APO PATCHONE, about 50 percent to about 90 percent Citrl, about 1 percent to about 10 percent GERALDEHYDE, about 5 percent to about 20 percent Limonene PFG, about 5 percent to about 15 percent PEOMOSA, and about 0 percent to about 5 percent VIOLIFF, wherein the percentages are weight percentages. One suitable mixture comprises about 1 percent APO PATCHONE, about 75 percent Citral, to about 0.5 percent GERALDEHYDE, about 15 percent Lirnonene PFG, about 7.5 percent PEOMOSA, and about 1 percent VIOLIFF.

Another suitable liquid material with which the substrate 50 can be impregnated comprises at least about 15 percent GERALDEHYDE, and in one embodiment between about 15 and about 30 percent GERALDEHYDE. Yet another suitable material between about 50 and about 100 percent GERALDEHYDE, with the balance being perfume.

The structures of the present invention can have a substrate 50 impregnated with an initial loading of about 2.0 grams or less of the volatile liquid material, and in one embodiment about 1.0 grams or less. The ratio of the weight of the initial loading of the volatile liquid material to the weight of the dry substrate should be art least about 0.1. In one embodiment, the ratio of the weight of the initial loading of the volatile liquid material to the weight of the dry substrate 50 is preferably at least about 2.0, and in one embodiment at least about 4.0.

The structures of the present invention can provide an effective release rate of insect repellent material with a relatively small amount of insect repellent material. Without being limited by theory, it is believed that the ability of the structures of the present invention to provide an effective release rate with a small amount of insect repellent is due, at least in pat, to having a relatively high ratio of weight of the initial loading of insect repellent material to dry substrate weight.

Figure 8:
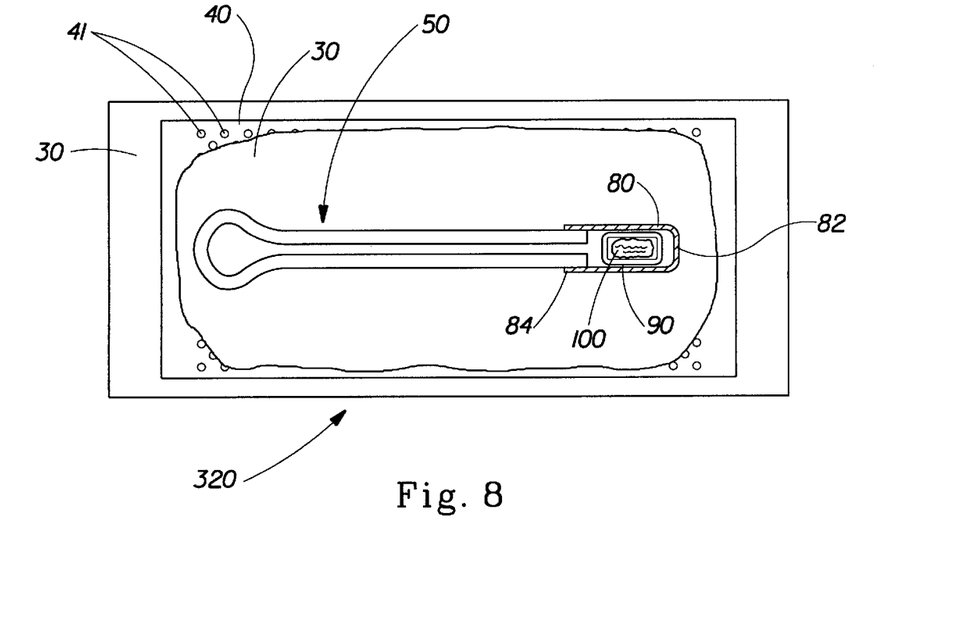
FIG. 8 is an alternative embodiment of the present invention having a substrate formed of a strand of woven polyolefinic fibers and as breakable vessel connected to the substrate through a fluid conduit.

In the embodiment shown in FIG. 1, the substrate 50 can be impregnated with the volatile liquid material, and then sealed in the wrapper 22. In an alternative embodiment shown in FIGS. 5 and 8, the article 20 can comprise a liquid impermeable breakable vessel 90 containing a predetermined quantity of the volatile liquid 100, and a substrate 50 for receiving the predetermined quantity of volatile liquid 100. The breakable vessel 90 is breakable by a user to direct the volatile liquid 100 to the substrate 50. The breakable vessel maintains the volatile liquid material separate from the substrate 50 until the article 20 is ready to be used. Accordingly, the volatile liquid substance is less likely to evaporate from the article 20 prior to the time the article is placed in use.

The breakable vessel 90 can comprise a packet formed from a liquid impervious layer of material. For instance, the vessel 90 can comprise a packet formed from a polymeric film, such as a thermoplastic film. Such a packet can also be formed from a laminate of foil and a polymeric film. Suitable materials from which the vessel 90 can be formed include the films and laminate from which the barrier layer 30 can be formed, as described above. In one embodiment, the vessel 90 can be formed from a film manufactured by Tredegar Industries of Terre Haute, Indiana under the designation C-8570 and having a thickness of about 0.028 mm.

Figure 5:
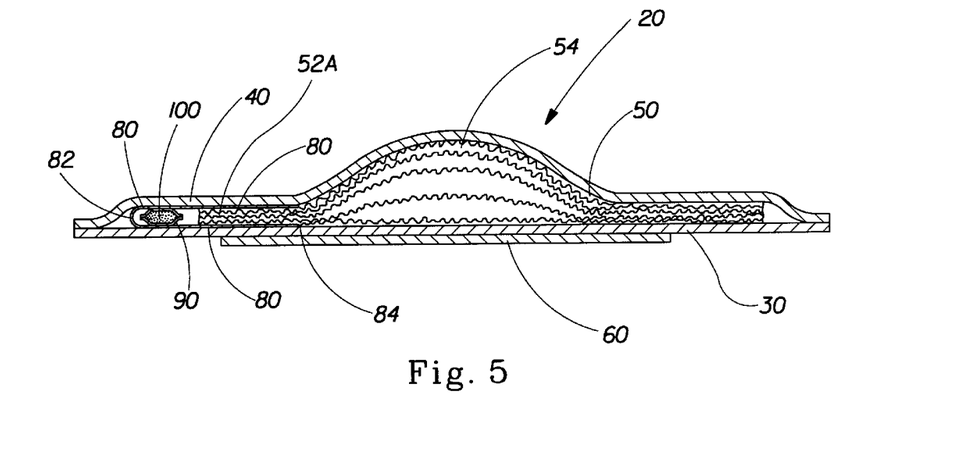
FIG. 5 is a cross-sectional view of an alternative embodiment of the present invention having a breakable vessel containing the volatile liquid insect repellent positioned intermediate the porous cover layer and the barrier layer.

The breakable vessel 90 and at least a portion of the substrate 50 can be disposed in a fluid conduit. The fluid conduit directs the predetermined amount of volatile liquid 100 from the vessel 90 to the substrate 50, once the vessel 90 is broken. In FIG. 5, the fluid conduit comprises a sleeve 80 having a closed end 82 and an open end 84. The vessel 90 is disposed in the sleeve 80 adjacent the closed end 82. At least a portion of the relatively high density region 52A of the substrate 50 extends into the open end 84 of the sleeve 80. Generally parallel capillary channel fibers 55 in the region 52A extend into the sleeve 80 to wick fluid from the broken vessel 90 to the relatively low density region 54.

The sleeve 80 can be joined to the substrate 50 to form a fluid seal. For instance, the open end 84 of the sleeve 80 can be adhesively joined to the substrate 50 to prevent the predetermined amount of liquid 100 from flowing between the substrate 50 and the sleeve 80. The sleeve can be formed of a liquid impermeable film, such as a polymeric film which is substantially non-absorbent with respect to the volatile liquid substance. Suitable materials from which the sleeve can be formed include those films and laminate from which the barrier layer 30 can be formed. Another suitable film from which the sleeve 80 can be formed is SARAN brand wrap manufactured by Dow Brands, Inc. of Indianapolis, Ind.

In another embodiment, the substrate 50 can comprise a nonwoven web of paper fibers, including paper webs manufactured by through air drying techniques as, well as by conventional papermaking techniques. Suitable webs from which the substrate 50 can be formed are disclosed in the following U.S. Patents, which are incorporated herein by reference: U.S. Pat. No. 4,528,239 issued Jul. 9, 1985 to Trokhan; U.S. Pat. No. 5,277,761 issued Jan. 11, 1994 to Phan et al.; and U.S. Pat. No. 5,245,025 issued Sep. 4, 1993 to Trokhan et al. In one embodiment, the substrate 50 can have a weight of between about 0.20–0.40 grams, and can comprise 2 or more sections of 2-ply paper towels cut from BOUNTY brand paper towels manufactured by The Procter and Gamble Company.

Figure 10:
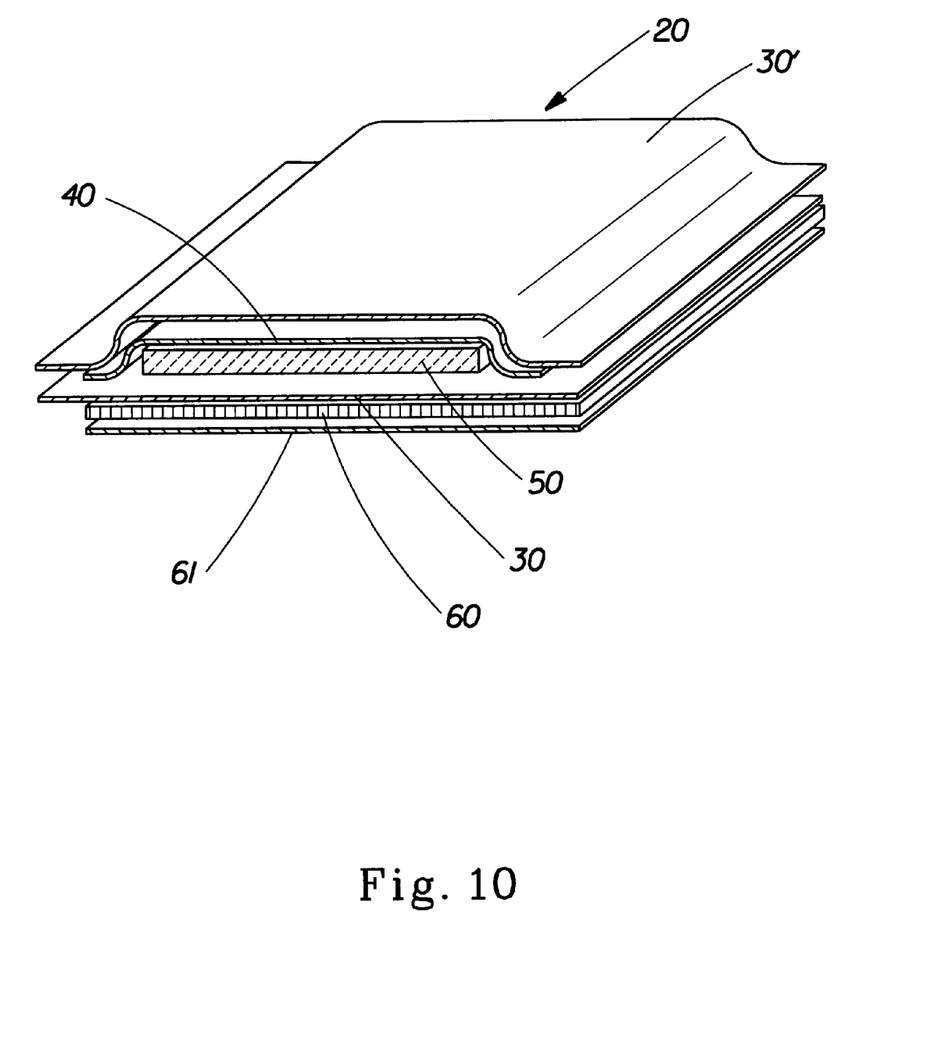
FIG. 10 is an alternative embodiment of the present invention wherein a peelable top film is heat sealed to at least portions of the barrier layer to prevent evaporation of the liquid material prior to use of the article.

FIG. 10 illustrates an example of article 20 according to the present invention. The article 20 includes a substrate 50 measuring about 2.5 inch by 2.5 inch, and having a dry weight of about 0.30–0.35 grams. The substrate comprises two layers, one overlying the other, and each layer comprising a 2.5 inch by 2.5 inch section cut from a two ply BOUNTY brand paper towel. The substrate 50 is impregnated with about 1.5 grams of a volatile liquid material comprising one or more of the ingredients listed above.

The substrate 50 is disposed between the LAFF porous cover layer 40 described above, and a barrier layer 30. The cover layer 40 measures about 2.9 inch by about 2.9 inch, and the barrier layer 30 measures about 3.25 inch by about 3.25 inch. The barrier layer 30 comprises a generally transparent laminate film. A transparent film is desirable to minimize the visibility of the article 20, as worn. The laminate film comprising layers of Polyethylene Terephthalate (PET), Ethyl Vinyl Alcohol (EVOH), and Low Density Polyethylene (LDPE). Such a laminate film is available from the Curwood Co. of New London, Wis. The LDPE layer of the barrier layer 30 can be joined to the porous cover layer 40 by an adhesive or by heat A peelable top film 30' has its perimeter releasably heat sealed to the perimeter of barrier layer 30 extending beyond the edges of the porous cover layer 40. The peelable top film 30' comprises a laminate of PET, aluminum foil, Nylon 6, and Surlyn. The Surlyn face of the top film 30' faces the LDPE surface of the barrier layer 30, and can be melted to provide a peelable heat seal between the top film 30' and the barrier layer 30. The heat seal joining the top film 30' to the barrier layer 30 is about 3/16 inch wide. The heat seal provides releasable attachment of the peelable top film 30' to the barrier layer 30. Together, the top film 30' and the barrier film 30 provide a sealed compartment which prevents evaporation of the volatile liquid material from the substrate 50.

The article in FIG. 10 has a fastener 60 joined to the outwardly facing surface of the barrier layer 30. The fastener 60 comprises a layer of pressure sensitive adhesive joined to the barrier layer 30. A release paper cover 61 having an inwardly facing, silicone covered surface is positioned over the outwardly facing surface of the layer of pressure sensitive adhesive prior to attachment of the article, to the target surface. The total weight of the article 20, including the volatile liquid material, but not counting the weight of the release paper cover 61 and the peelable top film 30', is about 3.3 grams. The length, width, and thickness of the article (thickness measured using a 0.95 inch load foot and 32.2 gram load) are about 3.25 inch, 3.25 inch, and about 2.7 mm, respectively.

The articles of the present invention can have a stiffness of no more than about 0.5 lb/in, and preferably no more than about 0.1 lb/in when measured using a three point bending test. The three point bending test is conducted using a suitable tensile testing machine, such as an INSTRON brand Model 1122 tester fitted with a 2 kg, compressive load cell. To measure the stiffness of the article 20, the article 20 is supported on two horizontal plates spaced 1.0 inch apart, so that the article bridges the 1.0 inch gap between the two horizontal plates (the 1.0 inch gap measured parallel to the length of the article). A 1/8 inch thick plate is supported on the tester cross head so that, as the cross head moves downward, the edge of the 1/8 inch thick plate moves downward and contacts the article midway along the article's length, thereby pushing the article into the gap between the two horizontal plates. The cross head moves at a rate of 1 inch per minute. The peak load measured as the cross-head travels downward is recorded. The peak load is divided by the width of the article to obtain the stiffness of the article in lb/in.

The stiffness of the articles such as those shown in FIG. 10 was measured using the procedure above. The peak loads recorded ranged between about 0.09 lb to about 0.19 lb, which for the articles' width of 3.25 inch, corresponds to a three point bending stiffness of between about 0.03 lb/in and 0.06 lb/in.

CONTACT WETNESS MEASUREMENT

The contact wetness of the release surface of the article 20 is measured by pressing the article and a piece of filter paper with a confining pressure of 1.0 psi for a period of 10 seconds, and measuring the amount of the liquid material which is; transferred from the article to the filter paper. The filter paper is Filter Paper Grade #989 manufactured by the Ahlstrom Filtration Co. of Mt Holly Springs. Filter Paper Grade #989 has a Cellulose fiber composition and a white, unfinished surface. The filter paper has a basis weight of 137 grams per square meter, a thickness of 0.70) mm, a Frazier Permeability of 39 cfm/square foot, a capillary rise of 87 mm/minute, is and a retention of 55 micrometers. The contact wetness is measured at a temperature of about 70 degrees plus or minus 2 degrees, and a relative humidity of about 55 percent.

If the article comes with a wrapper (the substrate is pre-impregnated), the contact wetness is measured as follows. A piece of the filter paper is cut to have length and width dimensions as large as those of the substrate 50. The dry filter paper is weighed. The wrapper sealing the article 20 is removed, and the article is immediately placed on a flat, horizontal surface with the release surface facing upwards. The filter paper is then placed over the release surface of the article to be positioned above the substrate 50. A weight is gently lowered onto the filter paper to apply a uniform pressure loading of 1.0 psi over the substrate (The weight is selected so that the weight divided by the product of the length and width of the substrate, as viewed in FIG. 2, equals 1.0 psi). The pressure loading is maintained for 10 seconds, after which the weight is removed and the filter paper is immediately reweighed. The difference between the second and first weights of the filter paper is the contact wetness for the sample. The normalized contact wetness of the sample is the contact wetness divided by the weight of liquid material originally impregnating the substrate.

If the substrate is not pre-impregnated (such that the volatile liquid material must be applied to the substrate by the user prior to use of the article), then the above procedure is used, with the following modification. The volatile liquid material is applied to the substrate. The article is then maintained on a flat, horizontal surface with the release surface facing upwards for 10 minutes to allow the liquid material to be distributed throughout the substrate. After 10 minutes, the filter paper is placed over the release surface, and the loading pressure is applied.

RELEASE RATE MEASUREMENT

The release rate of an article having volatile liquid material is measured using the following procedure. The release rate is measured in a KEM PONENT brand, fume hood chamber measuring about 4 foot by 3 foot by 4 foot and manufactured bad Kewaunee Scientific Corp of Adrian, Mich. The chamber is used with the vent open, the fan turned on, and the glass shield raised to the open position. The chamber provides an air speed of about 150 ft/min, as measured using a Vaneometer manufactured by the Dwyer Instrument Co. of Michigan City, Ind. The chamber is maintained at a temperature of about 70 degrees Fahrenheit, plus or minus 2 degrees. The pressure in the chamber is maintained at about 1 atmosphere and the relative humidity in the chamber is maintained at about 55 percent. A ring stand is positioned in the chamber to support articles for which the release rate is to be measured.

For articles having a substrate pre-impregnated with a volatile liquid material and sealed to prevent evaporation of the volatile liquid material, the release rate is determined using the following measurements.

The seal preventing evaporation is removed, and the article is immediately weighed on a balance located in the chamber to obtain a beginning article weight, or WB, in grams. The article is then supported on the ring stand in the chamber. After one hour, the article is again weighed on the balance. This weight is the one-hour article weight, W1. The article weight is re-measured at one-hour intervals to obtain the two-hour article weight, W2; the three-hour article weight, W3; and the four hour article weight, W4. The article is supported on the ring stand in the chamber between each weight measurement.

After four hours, the article is supported on the ring stand and periodically reweighed until substantially all the volatile material has escaped from the article, such that there is no significant change in the weight of the article on subsequent reweighings at one hour intervals. The weight of the article at this point is the dry article weight, WD.

The macroscopic space area of the substrate 50 which was wetted by the volatile liquid material is designated SA, and is measured in square inches. Fly macroscopic surface area, it is meant the surface area of the substrate calculated from the perimetric dimensions (e.g. width and length) of the substrate, as differentiated from the micro-surface area of individual fibers or filaments making up the substrate. The surface area SA is measured when the substrate is substantially dry.

Those portions of the surface area of the substrate which are sealed (such as by a sleeve 80) so that they cannot release the volatile liquid material are not counted in the area measurement SA. If the article being measured has a porous cover layer 40, the surface area SA is the portion of the surface area of the substrate which underlies the porous cover layer 40 and which is capable of releasing the volatile, [] liquid material (i.e. not sealed, such as by a sleeve 80).

By way of example, the surface area SA of the substrate 50 shown in FIGS. 1–2 would be the combined surface areas of the regions 52A, 52B, and 54 underlying the porous cover 40, as is viewed in FIG. 2. In the embodiment shown in FIG. 5, the surface area SA would not include the portion of region 52A covered by sleeve 80.

For articles having a substrate which is not pre-impregnated with a volatile liquid material, the release rate is determined from the following measurements. The macroscopic surface area, SA, of the dry substrate is measured. The dry article weight, WD, is measured with a balance. The article is then impregnated with the volatile liquid material, and immediately weighed with a balance to obtain the beginning article weight, WB. The article is then supported on the ring stand in the chamber. After one hour, the article is again weighed on the balance. This weight is the one-hour article weight, WI. The article weight is re-measured at one-hour intervals to obtain the two-hour article weight, W2; the three-hour article weight, W3; and the four hour article weight, W4. The article is supported on the ring stand in the chamber between each weight measurement.

The release rate of articles having pre-impregnated and non-preimpregnated substrates can be calculated as follows. The weight of the volatile liquid material initially on the article is WL and is equal to WB–WD, in grams. The one-hour release rate of the article is the weight (WB–WI), in grams, of volatile liquid material released in the first hour, per square inch of surface area SA of the substrate, leer gram of volatile liquid material initially on the article.

The one-hour release rate R1 is calculated as:

(WB-W1 grams)/[(WL grams)×(SA square inches)-hr]

The two hour release rate, R2, can be calculated as follows:

(W1–W2 grams)/[(WL grams)×(SA square inches)-hr ]

The three hour release rate, R3, can be calculated as follows:

(W2–W3 grams) /[(WL grams)×(SA square inches)-hr]

The extended four hour release rate, R4, can be calculated as follows:

(W3–W4 grams)/[(WL grams)×(SA squae inches)-hr]

In one embodiment, the present invention provides an extended four hour release rate R4 which is at least about 50 percent, and more preferably at least about 80 percent of the one-hour release rate R1.

In order to determine a normalized release rate for an article 20, the following measurements are made. A petri dish having a depth of about 0.47 inch and an inner diameter of 1.7 inch (to provide a petri she area SP of 2.27 square inches) is weighed to provide a weight of the clean, empty dish, WP. About 1.5 to about 2.0 grams of the same liquid with which the substrate 50 is impregnated is added to the dish, so that the bottom of the dish is covered. The petri dish and liquid are immediately weighed to provide WBP, the beginning weight of the dish and liquid. The initial liquid weight is WLP=WBP–WP. The dish is placed in the flume hood chamber under the same conditions described above with respect to measuring the release rates of the article 20. After one hour, the dish is weighed on the balance. This weight is the one-hour weight, WP1. The petri release rate RP is:

RP=(WBP-WP1) grams /[(WLP grams×(SP) square inches-hr]

The normalized one hour release rate R1N is the ratio of the release rate R1 divided by the one hour petri release rate RP, or R1N=R1/RP. Similarly, the normalized two, three, and four hour release rates are R2/RP, R3/RP, and R4/RP.

Table 1 below lists Contact Wetness test results for different disposable patch constructions, the dfferent patch types designated A–F. Patches A–E are articles according to the present invention. Patch type F is a commercially available REPELLO-PATCH brand patch, described below.

Table 2 below lists release rate test results and normalized release rate test results for patch constructions A–E.

TABLE 1

| Contact Wetness (CW) | |
|---|---|
| A. Substrate (50): | 2.5" × 2.5", 2 layers Bounty Towel |
| Liquid: | 1.5 gm GERALDEHYDE |
| Cover Layer(40) | LAFF |
| CW (n = 5) | 1.7 mg, 0.5 mg, 0.8 mg 1.0 mg, 1.9 mg/mean 1.3 mg |
| Normalized CW | 0.87 mg/gram |
| B. Substrate (50): | 1.5" × 4", 2 layers Bounty Towel |
| Liquid | 2.0 gm Citronella Ceylon |
| Cover Layer (40) | LAFF 38 percent open area |
| CW (n = 5) | 29 mg, 17 mg, 20 mg, 15 mg, 23 mg/mean 21 mg |
| Normalized CW | 10.5 mg/gram |
| C. Substrate (50): | 1.5" × 4", 2 layers Bounty Towel |
| Liquid | 2.0 gm Citronella Ceylon |
| Cover Layer (40) | Always Ultra Topsheet (DRI-WEAVE) |
| CW (n = 3) | 25 mg, 20 mg, 27 mg/mean 24 mg |
| Normalized CW | 12.0 mg/gram |

TABLE 1-continued

Contact Wetness (CW)

| | | |
|---|---|---|
| D. | Substrate (50): | 1.5" × 4", 2 layers Bounty Towel |
| | Liquid | 2.0 gm Citronella Ceylon |
| | Cover Layer (40) | MOLDEX sheet |
| | CW (n = 3) | 1.0 mg, 0.5 mg, 0.5 mg, 1.1 mg, 1.3 mg/mean 0.9 mg |
| | Normalized CW | 0.5 mg/gram |
| E. | Substrate (50): | 1.5" × 4", 2 layers Bounty Towel |
| | Liquid | 2.0 gm Citronella Ceylon |
| | Cover Layer (40) | 3M Blenderm Brand Surgical Tape no. 1525 |
| | CW (n = 5) | 29 mg, 17 mg, 20 mg, 15 mg, 23 mg/mean 21 mg |
| | Normalized CW | 10.5 mg/gram |
| F. | Substrate(50) | REPELLO-PATCH BRAND |
| | LIQUID | average of about 0.73 gm Citronella- |
| | Cover Layer | None |
| | CW (n = 5) | 0.51 gm, 0.35 gm, 0.40 gm, 0.39 gm, 0.36 gm/mean 0.40 gm |
| | Normalized CW | 0.55 gram/gm or (550 mg/gm) |

TABLE 2

Release Rates

RP (Geraldehyde, 1.5 gm in dish, n = 5) = 2.64 mg/gm-square inch-hr
A. Substrate (50):    2.5" × 2.5", 2 layers Bounty Towel
   Liquid:            1.5 gm GERALDEHYDE
   Cover Layer(40)    LAFF
Release Rates (mg/gm-square inch-hr) (n = 5)
   R1: 1.07   R2: 1.39   R3: 0.83   R4: 0.83   R4/R1 = 0.77
Normalized Release rates (dimensionless) based on RP = 2.64
   R1N: 0.40   R2N: 0.53   R3N: 0.31   R4N: 0.31
RP (Citronella Ceylon, 2.0 gm in dish, n = 5) = 28.4 mg/gm-square inch-hr (n = 5)
B. Substrate (50):    1.5" × 4", 2 layers Bounty Towel
   Liquid             2.0 gm Citronella Ceylon
   Cover Layer (40)   LAFF 38 percent open area
Release Rates (mg/gm-square inch-hr) (n = 2)
   R1: 19.0   R2: 13.2   R3: 9.4   R4: 6.5   R4/R1 = 0.34
Normalized Release rates (dimensionless) based on RP = 28.4
   R1N: 0.67   R2N: 0.46   R3N: 0.33   R4N: 0.23
C. Substrate (50):    1.5" × 4", 2 layers Bounty Towel
   Liquid             2.0 gm Citronella Ceylon
   Cover Layer (40)   Always Ultra Topsheet (DRI-WEAVE)
Release Rates (mg/gm-square inch-hr) (n = 2)
   R1: 16.2   R2N: 10.6   R3: 6.6   R4: 5.7   R4/R1 = 0.35
Normalized Release rates (dimensionless) based on RP = 28.4
   R1N: 0.57   R2N: 0.37   R3N: 0.23   R4N: 0.20
D. Substrate (50):    1.5" × 4", 2 layers Bounty Towel
   Liquid             2.0 gm Citronella Ceylon
   Cover Layer (40)   MOLDEX sheet
Release Rates (mg/gm-square inch-hr) (n = 2)
   R1: 11.1   R2: 9.5   R3: 6.4   R4: 1.9   R4/R1 = 0.17
Normalized Release rates (dimensionless) based on RP = 28.4
   R1N: 0.39   R2N = 0.33   R3N: 0.22   R4N: 0.07
E. Substrate (50):    1.5" × 4", 2 layers Bounty Towel
   Liquid             2.0 gm Citronella Ceylon
   Cover Layer (40)   3M Blenderm Brand Surgical Tape no. 1525
Release Rates (mg/gm-square inch-hr) (n = 2)
   R1: 6.2   R2: 6.1   R3: 5.4   R4: 1.6   R4/R1 = 0.26
Normalized Release rates (dimensionless) baeed on RP = 28.4
   R1N: 0.22   R2N: 0.21   R3N: 0.19   R4N: 0.06

One and two-hour release rates were also measured for a first sample of a commercially available bug repellent patch marketed as REPELLO-PATCH by P.J. Maxwell. The sample REPELLO-PATCH tested had a dry, uncovered substrate having a surface area SA of about 3.5 square inches and a separately packaged liquid material which was added to the substrate. The separately packaged liquid material was labeled as being 99 percent citronella. About 0.75 grams of the separately packaged liquid material was added to the substrate. The one hour release rate was determined to be about 0.0098 grams/square inch-gram-hour, and the two hour release rate was determined to be about 0.0074 grams/square inch-gram-hour. One, two, three, and four-hour release rates for a second sample of a REPELLO-PATCH brand path were also measured, with the following results in grams/square inch. gram-hour: 0.0048, 0.0040,0.0036, and 0.0034.

In the embodiments described, the substrate 50 is impregnated with substance effective for repelling insects. In other embodiments, the substrate 50 can be: impregnated with materials which are effective in providing a desired fragrance, such as perfume materials, or combinations of such materials.

While particular embodiments of the present invention have been illustrated and described, it would be obvious to those skilled in the art that various changes and modifications can be made without departing from the spirit and scope of the invention. It is intended to cover, in the appended claims, all such modifications and intended uses.

What is claimed is:

1. A portable, disposable article for providing release of a volatile liquid material from a release surface of the article, the article comprising a porous cover layer, wherein the cover layer comprises a formed film having a plurality of three-dimensionally formed tapered apertures, the cover layer covering a substrate impregnated with the volatile liquid material, wherein the volatile liquid material is selected from the group consisting of citronellol, citronellal, citronellyl nitrile, para-Isopropylcyclohexanol, 3,7-dimethyl-2,6-Octadien-1-al, 5,9-dimethyl-4,8-decadienal, p-Mentha-1,8-diene, o-methyl betarhenylethyl alcohol, 4-Cyclooctenyl methyl carbonate, ethyl butylacetylaminopropionate, dimethyl phthalate, thyme oil red, gamma methyl ionone, beta phenylethyl alcohol, clove bud oil, and mixtures thereof.

2. The portable disposable article of claim 1 wherein the release surface has a contact wetness of less than about 50 mg.

3. The portable disposable article of claim 2 wherein the release surface has a contact wetness of less than about 25 mg.

4. The portable disposable article of claim 1 wherein the release surface has a normalized contact wetness of less than about 100 mg/gram.

5. The portable disposable article of claim 4 wherein the release surface has a normalized contact wetness of less than about 25 mg/gram.

6. The portable disposable article of claim 1 wherein the article has a normalized release rate of at least about 0.25.

7. The article of claim 6 wherein the article has a normalized release rate of at least about 0.40.

8. The article of claim 7 wherein the article has a normalized release rate of at least about 0.50.

9. The article of claim 1 wherein the article has a substrate impregnated about 2.0 grams or less of the volatile liquid material.

10. The article of claim 9 wherein the ratio of the weight of the volatile liquid material to the weight of the substrate is at least about 2.0.

11. The article of claim 1 wherein the article has a maximum caliper no greater than about 3.0 mm.

12. A portable, disposable article for providing release of a volatile liquid material, the article comprising:
   a porous cover layer wherein the cover layer comprises a formed film having a plurality of tapered apertures for providing release of the volatile liquid material from the article,
      wherein the porous cover layer has an open area ratio of at least about 20 percent, and wherein the porous cover layer has a contact wetness of less than about 100 mg;

a barrier layer, the barrier layer being generally impervious to the volatile liquid material; and a substrate impregnated with the volatile liquid material, wherein at least a portion of the substrate is disposed intermediate the porous cover layer and the barrier layer.

13. A portable, disposable article for providing controlled release of a volatile liquid material, the article comprising:

a substance impregnated with a volatile liquid material selected from the group consisting of citronellol, citronellyl nitrile, 3,7-dimethyl-2,6-Octadien-1-al, 5,9-dimethyl-4,8-decadienal, p-Mentha-1,8-diene, o-methyl betaphenylethyl alcohol, 4-Cyclooctenyl methyl carbonate, ethyl butylacetylaminoproiionate, dimethyl phthalate, thyme oil red, gamma methyl ionone, beta phenylethyl alcohol, clove bud oil, and mixtures thereof; and a liquid impermeable porous cover layer for providing release of the volatile liquid material from the article; and wherein the article has a normalized release rate of at least about 0.25, and wherein the porous cover layer has a contact wetness of less than about 100 mg.

14. The article of claim 13 wherein the porous cover layer has a contact wetness of less than about 50 mg.

15. The article of claim 14 wherein the release surface has a normalized contact wetness of less than about 25 mg/gram.

16. The article of claim 13 wherein the porous cover layer has an opening area ratio of at least about 20 percent.

17. The article of claim 16 wherein the porous cover layer has an opening area ratio of at least about 30 percent.

18. The article of claim 13 wherein the porous cover layer has a caliper of at least. about 0.015 inch.

19. The article of claim 18 wherein the porous cover layer has a caliper of at least about 0.050 inch.

20. The article of claim 13 wherein the article has a substrate impregnated with about 2.0 grams or less of the volatile liquid material.

21. The article of claim 20 wherein the ratio of the weight of the volatile liquid material to the weight of the substrate is at least about 2.0.

22. The article of claim 13 wherein the article has a maximum caliper no greater than about 3.0 millimeter.

23. The article of claim 12 wherein the porous cover layer has an open area ratio of at least about 30 percent, and wherein the porous cover layer has a contact wetness of less than about 50 mg.

24. The article of claim 12 wherein the article comprises no more than about 2.0 grams of the volatile liquid material, and wherein the article has a normalized release rate of at least about 0.40.

25. The article of claim 23 wherein the ratio of the weight of the volatile liquid material to the weight of the substrate is at least about 2.0.

* * * * *

UNITED STATES PATENT AND TRADEMARK OFFICE
CERTIFICATE OF CORRECTION

PATENT NO.   : 6,162,454
DATED        : December 19, 2000
INVENTOR(S)  : Nicholas Albert Ahr et al.

Page 1 of 1

It is certified that error appears in the above-identified patent and that said Letters Patent is hereby corrected as shown below:

Column 2,
Line 35, "mn" should read -- mm --.
Line 38, "grants" should read -- grams --.

Column 5,
Line 4, "wearers skirt" should read -- wearer's skin --.
Line 10, "bee" should read -- be --.
Line 50, "et a." should read -- et al. --.
Line 56, "relatives" should read -- relative --.

Column 7,
Line 2, "tire" should read -- the --.

Column 13,
Line 20, "space" should read -- surface --.
Line 22, "Fly" should read -- By --.

Signed and Sealed this

First Day of January, 2002

Attest:

Attesting Officer

JAMES E. ROGAN
Director of the United States Patent and Trademark Office